US009204782B2

(12) United States Patent
Nguyen et al.

(10) Patent No.: US 9,204,782 B2
(45) Date of Patent: *Dec. 8, 2015

(54) MUCOSAL RESECTION DEVICE AND RELATED METHODS OF USE

(71) Applicants:Man Nguyen, West Roxbury, MA (US); Larry Stanton, Burlington, MA (US)

(72) Inventors: Man Nguyen, West Roxbury, MA (US); Larry Stanton, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 454 days.

This patent is subject to a terminal disclaimer.

(21) Appl. No.: 13/659,760

(22) Filed: Oct. 24, 2012

(65) Prior Publication Data

US 2013/0110109 A1 May 2, 2013

Related U.S. Application Data

(60) Provisional application No. 61/552,326, filed on Oct. 27, 2011.

(51) Int. Cl.
*A61B 17/94* (2006.01)
*A61B 1/00* (2006.01)
*A61B 17/3205* (2006.01)
*A61B 17/00* (2006.01)
*A61B 17/30* (2006.01)

(52) U.S. Cl.
CPC ......... *A61B 1/00089* (2013.01); *A61B 1/00087* (2013.01); *A61B 1/00101* (2013.01); *A61B 17/32056* (2013.01); *A61B 2017/00269* (2013.01); *A61B 2017/00296* (2013.01); *A61B 2017/308* (2013.01)

(58) Field of Classification Search
CPC ............... A61B 1/00101; A61B 1/018; A61B 2017/00296; A61B 17/00234; A61B 17/12013; A61B 17/221; A61B 17/32056; A61B 1/00059; A61B 1/00089; A61B 2017/00269; A61B 2017/00473
See application file for complete search history.

(56) References Cited

U.S. PATENT DOCUMENTS 6,059,719 A 5/2000 Yamamoto et al.
6,306,081 B1 10/2001 Ishikawa et al.
(Continued)

FOREIGN PATENT DOCUMENTS

JP 08-131397 5/1996
JP 09-066019 A 3/1997
JP 10-286224 A 10/1998
(Continued)

OTHER PUBLICATIONS

International Search Report for corresponding international application PCT/US2012/061735, dated Feb. 5, 2013 (5 pages).

*Primary Examiner* — Rex R Holmes
(74) *Attorney, Agent, or Firm* — Bookoff McAndrews, PLLC

(57) ABSTRACT

A resection device for resecting tissue from a body. The device includes an elongate member having a proximal end, a distal end, and a lumen extending from the proximal end to the distal end. The device further includes a cap assembly configured to be coupled to the distal end of the elongate member. The cap assembly may include a first cap defining a resection loop channel and a distal end having a first opening. The assembly may further include a second cap configured to receive a portion of the first cap. The second cap includes a distal end having a second opening. A distal portion of the first cap and a distal portion of the second cap may cooperate to define a resection loop track for receiving a resection loop.

20 Claims, 7 Drawing Sheets

(56) References Cited

U.S. PATENT DOCUMENTS

2004/0158124 A1* 8/2004 Okada ............................ 600/104
2013/0172918 A1* 7/2013 Smith et al. ................... 606/170

FOREIGN PATENT DOCUMENTS

| JP | 2010-022697 A | 2/2010 |
|----|---------------|--------|
| JP | 2010-042084 A | 2/2010 |

* cited by examiner

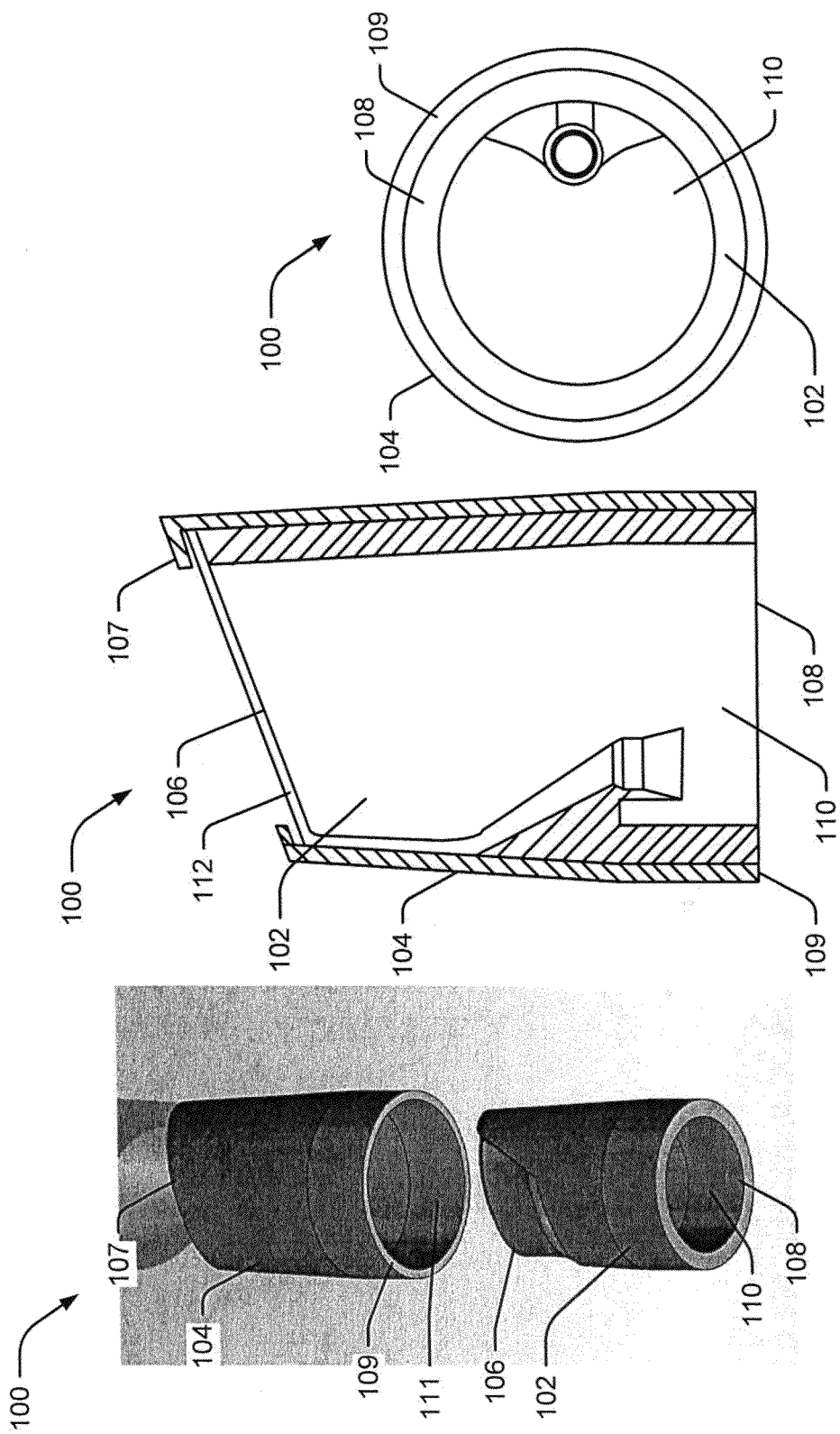

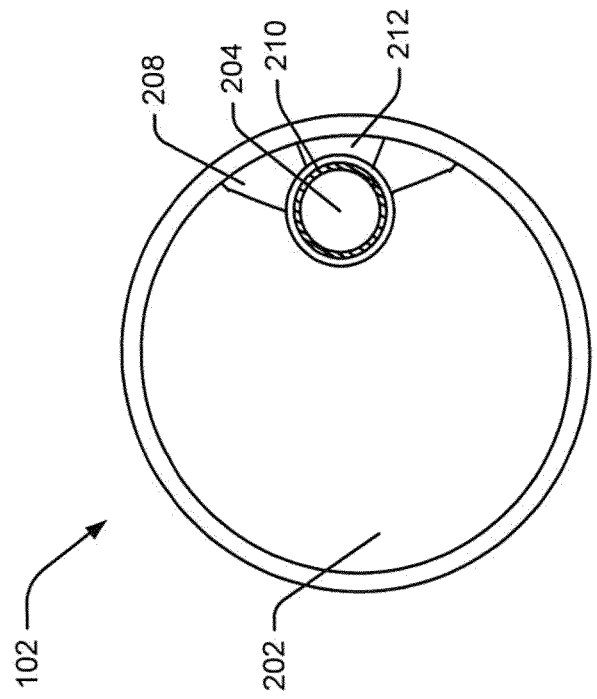
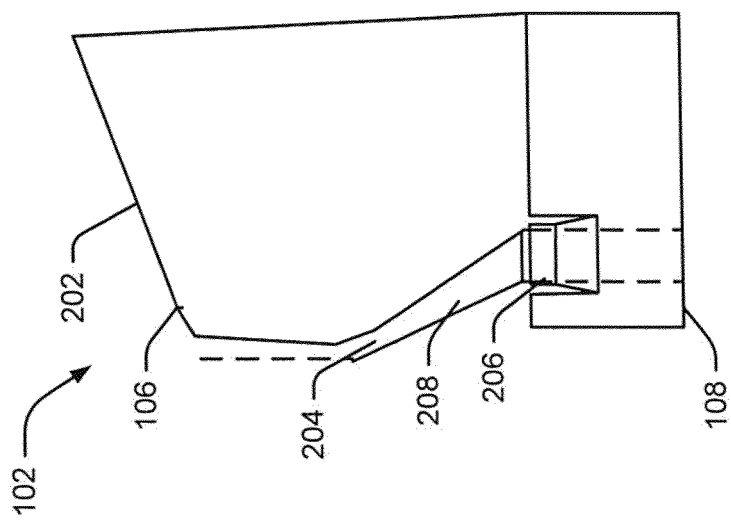
FIG. 2B
FIG. 2A

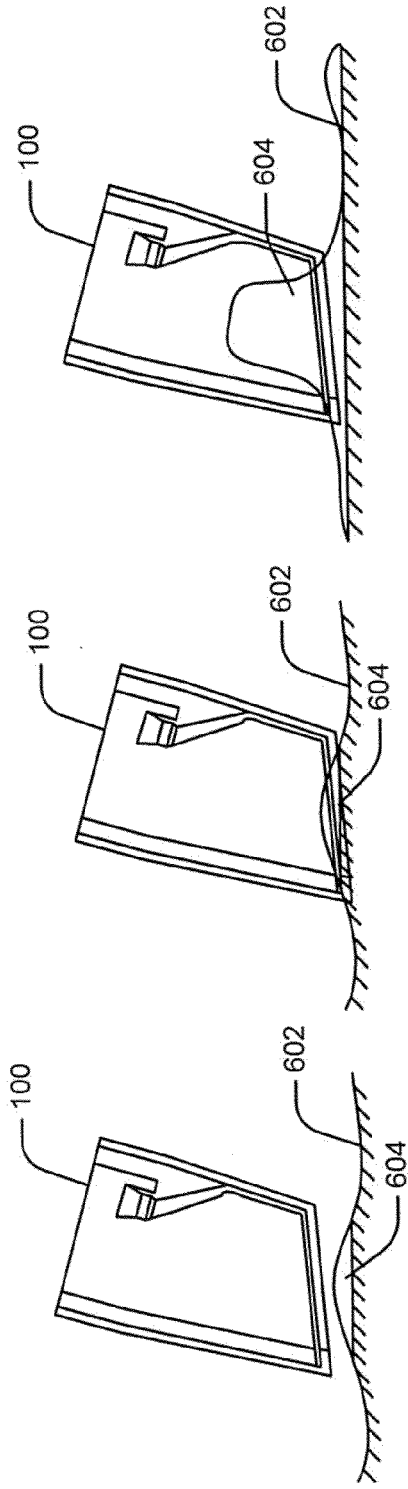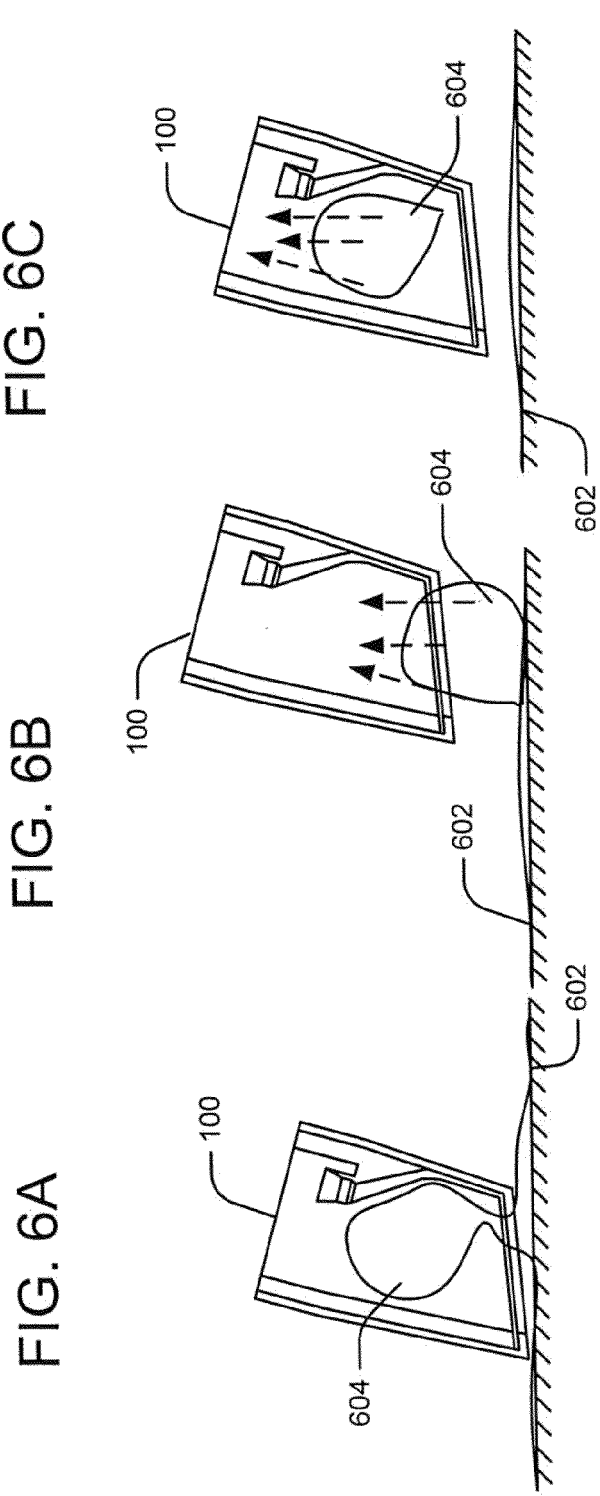

MUCOSAL RESECTION DEVICE AND RELATED METHODS OF USE

PRIORITY

This application claims priority to U.S. Provisional Application No. 61/552,326 filed on Oct. 27, 2011, the entire contents of which are incorporated herein by reference.

FIELD OF THE INVENTION

This disclosure relates generally to systems and methods for resecting tissue. More particularly, embodiments of the claimed invention relate to systems for endoscopic mucosal resection.

BACKGROUND OF THE INVENTION

Organ walls are composed of several layers: the mucosa (the surface layer), the submucosal, the muscularis (muscle layer), and the serosa (connective tissue layer). In gastrointestinal, colonic, and esophageal cancer, small polyps or cancerous masses form along the mucosa and often extend into the lumens of the organs. Conventionally, that condition has been treated by cutting out a portion of the affected organ wall. This procedure, however, may cause extensive discomfort to patients, and posed health risks. Recently, physicians have adopted a minimally invasive technique called endoscopic mucosal resection (EMR), which removes the cancerous or abnormal tissues (polyps) or normal tissues, keeping the walls intact.

EMR is generally performed with an endoscope, which is a long, narrow tube equipped with a light, video camera, and channels to receive other instruments. During EMR, the endoscope is passed down the throat or guided through the rectum to reach a tissue in the affected organ or otherwise targeted tissue. The distal end of the endoscope, further equipped with a cap that has a small wire loop, is guided towards the abnormality. Once there, a suction pump attached to the tube is started to draw the abnormality towards the endoscope cap. When the tissue is sufficiently drawn into the cap, the wire loop closes around the tissue, resecting it from the organ wall. Subsequently, excised tissue may be extracted by, e.g., the vacuum, for examination or disposal.

Certain polyps, such as pedunculated polyps, may be characterized by a stalk attached to the mucosal layer. Drawing such polyps into the cap without drawing in any other tissue is readily accomplished. Certain other polyps, such as sessile polyps, however, may exhibit a broad base and they lay flat on the mucosal surface, devoid of a stalk. It is often difficult to grasp these polyps without drawing in a part of the muscularis layer.

To overcome this problem, saline solution is typically injected beneath the target tissue to raise the mucosal tissue and create a buffer layer. The raised tissue can then readily be severed with a resection loop, often in several segments (segmental resection) depending on the size and location of the tissue.

In addition, the depth of the cut made by the wire loop cautery is critical. As discussed above, if the cut is too deep, the muscularis layer may be injured, which may further cause a perforation. Conversely, a cut too shallow may not remove enough of the affected tissue and therefore may require additional procedures or worse, contribute to the development of metastatic cancer. Typically, more than 2 mm of cancerous tissue clearance is required to assure complete removal. EMR, as performed with conventional devices and methods, may result in complications such as perforation, bleeding, and/or strictures, Therefore, there exists a need for an improved endoscopic mucosal resection loop that effectively resects pedunculated and sessile polyps or other tissues without damaging the surrounding tissue or muscle layers of the organ.

SUMMARY OF THE INVENTION

Embodiments of the present disclosure provide a device for resecting an undesired tissue from a patient's body using a minimally invasive surgical system.

In accordance with an aspect of the present disclosure, a resection device for resecting tissue from a body is described. The device includes an elongate member having a proximal end, a distal end, and a lumen extending between the distal end and the proximal end. The device further includes a cap assembly configured to be coupled to the distal end of the elongate member. The cap assembly includes a first cap defining a resection loop channel, wherein the first cap includes a distal end having a first opening. Further, the cap assembly includes a second cap configured to receive a portion of the first cap. The second cap includes a distal end that has a second opening, such that the distal portion of the first cap and a distal portion of the second cap cooperate to define a resection loop track for receiving a resection loop.

In various embodiments, the device may include one or more of the following additional features: the resection loop track and the resection loop channel may be in communication with each other; the resection loop track may be disposed in a plane parallel to a plane of the second opening; the resection loop track may extend at an angle to the resection loop channel; the resection loop channel may further include a cylindrical section positioned inside the first cap; the first cap includes a working channel extending from the distal end to the proximal end of the first cap; the resection loop channel may be formed of a flexible wall configured to collapse the resection loop channel when a resection loop is not present in the resection loop channel; a portion of the resection loop channel may be configured to prevent distal movement of a sheath associated with a resection loop; and the cap assembly may be configured to pivot relative to the distal end of the elongate member.

According to another embodiment, an endoscopic cap configured to be secured to a distal of an introduction sheath is described. The endoscopic cap includes a first cap defining a resection loop channel and having a distal end having a first opening. The endoscopic cap further includes a second cap having a distal end having a second opening. The second cap is configured to receive a portion of the first cap. Further, a distal portion of the first cap and a distal portion of the second cap cooperate to define a resection loop track for receiving a resection loop. The resection loop track may be in communication with the resection loop channel and disposed in a plane parallel to a plane of the second opening.

In various embodiments, the endoscopic cap may include one or more of the following additional features: the first cap includes a working channel extending from the distal end to the proximal end of the first cap; a portion of the resection loop channel is defined by an outer wall of the first cap; the resection loop channel further includes a cylindrical section disposed within the first cap; the distal end faces of the first and second caps may be angled relative to a longitudinal axis of the endoscopic cap; and the resection loop may be an electrocautery tool.

A further aspect of the present disclosure includes a cap assembly configured to be secured to a distal end of an endoscope. The cap assembly may include a first cap defining a resection device channel, wherein the first cap includes a distal end having a first opening. The cap assembly may also include a second cap configured to receive a portion of the first cap, wherein the second cap includes a distal end having a second opening, wherein a distal portion of the first cap and a distal portion of the second cap cooperate to define a resection device track for receiving a resection device.

In various embodiments, the method may include the additional features of: the resection device track and the resection device channel may be in communication with each other; the resection device track may extend at an angle to the resection device channel; the cap assembly may be configured to pivot relative to the endoscope; and the first cap may further include a working channel extending from the distal end to the proximal end of the first cap.

Additional objects and advantages of the claimed invention will be set forth in part in the description, which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIG. 1A is an exploded view of an EMR cap assembly, according to an embodiment of the present disclosure.

FIG. 1B is a sectional view of the EMR cap assembly of FIG. 1A.

FIG. 1C is an end view of the EMR cap assembly of FIG. 1A.

FIG. 2A is a schematic of an inner cap, according to embodiments of the present disclosure.

FIG. 28 is an end view of the inner cap of FIG. 2A.

FIGS. 6A-6F illustrate an exemplary method for resecting a tissue from an organ's mucosal wall using the EMR cap assembly of FIG. 1, according to embodiments of the present disclosure.

DESCRIPTION OF THE EMBODIMENTS

Figure 2D:
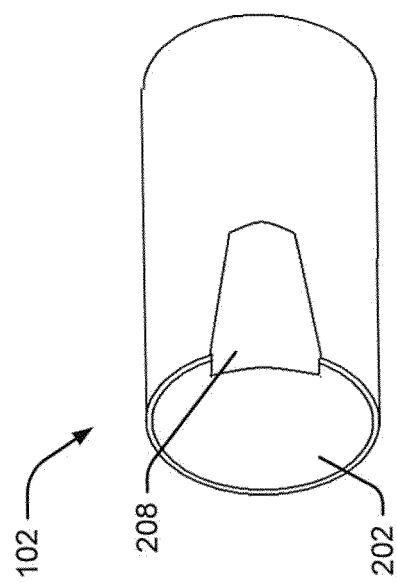
FIG. 2D is an isometric view of the inner cap of FIG. 2A taken from the distal end.

Reference will now be made in detail to embodiments of the present disclosure, an example of which is illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to systems and methods for resecting and extracting foreign or undesirable objects from a patient's body. For example, the device may remove cancerous polyps or lesions from the mucosal walls of the colon, esophagus, stomach, duodenum, or any other suitable location. It should be understood that the resection device may perform the functions of both resecting and retrieving, but for convenience, the term "resection device" will be used throughout this application.

The resection device may include an end-effector, such as, e.g., an EMR cap assembly, fitted on the distal end of any tube, such as an endoscope, for ensnaring, cauterizing, and extracting tissue such as a polyp. The EMR cap assembly may include a working channel, as well as a resection loop channel aligned with and inserted into the working channel. The EMR cap assembly may further include a track along its distal circumference in communication with the resection loop channel, such that a resection loop extending from the resection loop channel slides into the track when the resection loop is in an open position. In this position, the resection loop is parallel to the opening of the EMR cap assembly. When the EMR cap assembly is placed over an undesired tissue, suction can be applied to draw the tissue into the working channel. The resection loop may then be pulled proximally, reducing the diameter of the loop in the track and engaging the drawn tissue. Subsequently, the tissue is cauterized and extracted. Because the resection loop is parallel to the EMR cap assembly's distal opening, the operator can easily place the resection loop around the tissue to capture and cauterize it. Moreover, only the mass drawn into the EMR cap assembly's working channel is resected, ensuring that deeper layers of the organ wall are not affected.

In the following sections, embodiments of the present disclosure will be described using an exemplary body organ—the esophagus. It will be understood that this choice is merely exemplary and that the device may be utilized in any other suitable organ, such as the colon, duodenum, stomach, or any other organ that may be subject to polyps lesions, stones, and the like.

Exemplary Embodiments

Exemplary EMR Cap Assembly

FIGS. 1A-1C presents three views of an EMR cap assembly 100 for resecting polyps, lesions, or otherwise unwanted tissue from, e.g., the mucosal walls of organs according to embodiments of the present disclosure. EMR cap assembly 100 is configured to be secured to a distal portion of an endoscope for advancing towards a target location with a patient. Particularly, FIG. 1A is an exploded view, FIG. 1B is a sectional view, and FIG. 1C is an end view of EMR cap assembly 100. These figures will be commonly referenced to describe the structure and function of the EMR cap assembly 100. The EMR cap assembly 100 may be detachably connected to the distal end of any flexible or rigid tube, such as an endoscope used for colonoscopy, resectoscopy, cholangioscopy or mucosal resection.

EMR cap assembly 100 includes an inner cap 102 and an outer cap 104. The inner and outer caps 102, 104 may be hollow elongate members with distal ends 106, 107, respectively, and proximal ends 108, 109, respectively, with lumens 110, 111, respectively, extending between the respective distal and proximal ends. The outer cap 104 fits over the inner cap 102, and this complete assembly is attached, to a tube (not shown).

The inner cap 102 and outer cap 104 may have substantially circular cross-sections or cross-sections similar to those of body cavities. Where required by given applications, the EMR cap assembly 100 may include elliptical, semi-circular, rhombic, rectangular, or other non-circular profiles. Moreover, the diameter of the EMR cap assembly 100 may vary based on the size of the body lumens in which it operates. For example, if the EMR cap assembly 100 is inserted through the urethra, the diameter of the inner and outer caps may be very small. Conversely, if the device is inserted through the rectum, the diameter of the inner and outer caps may be larger.

Any suitable material may form inner and outer caps 102, 104. For instance, rigid or semi-rigid materials such as metals (including materials such as nitinol), polymers, resins, or plastics may be used. Further, a biocompatible material that does not irritate the body lumens may form a coating or layer over the outer surface of EMR cap assembly 100.

Figure 3C:
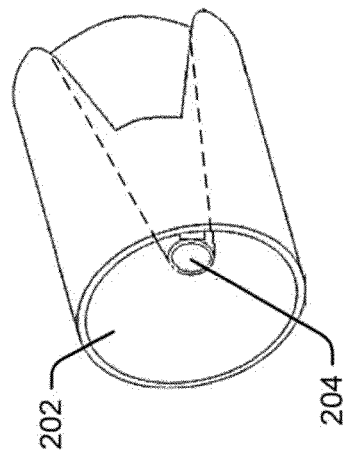
FIGS. 3A-3C illustrate various embodiments of the inner cap, according to embodiments of the present disclosure.
Figure 3B:
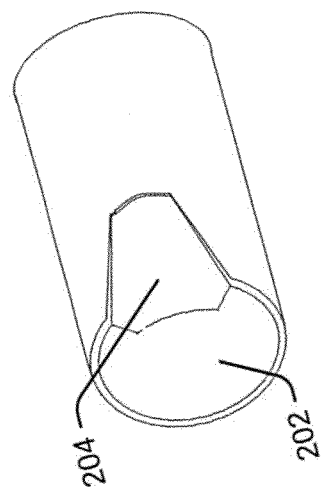
Figure 3A:
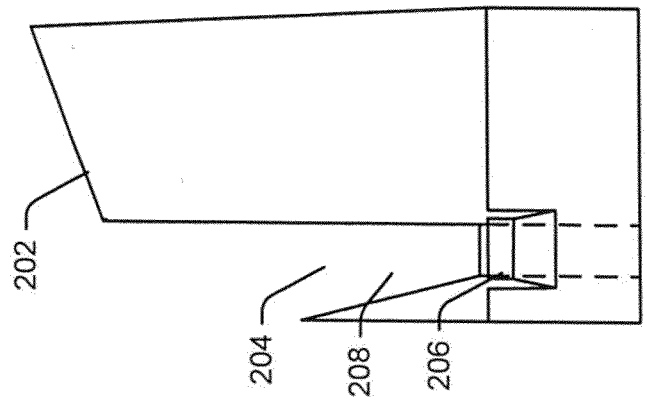
Figure 4:
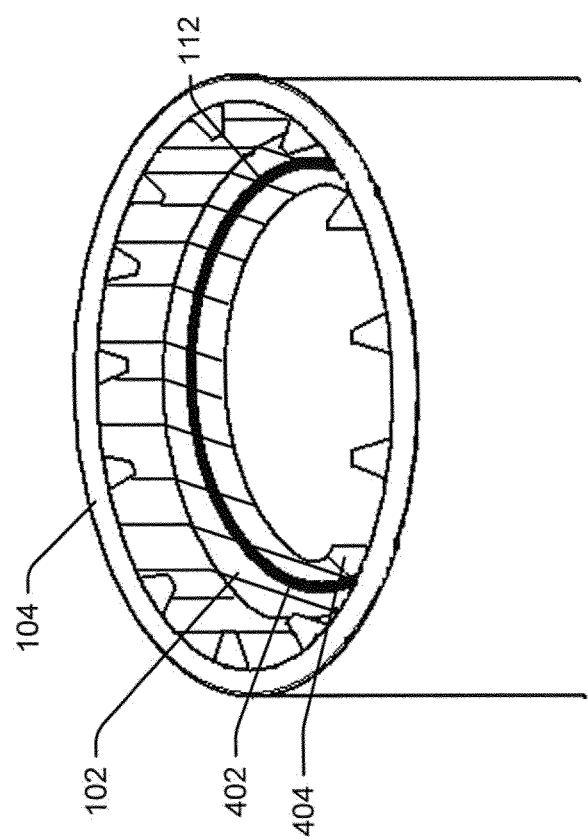
FIG. 4 illustrates the EMR cap assembly of FIG. 1 viewed from the distal end.

A detailed discussion of inner cap 102 and outer cap 104 follows, in connection with FIGS. 2-4.

Figure 2C:
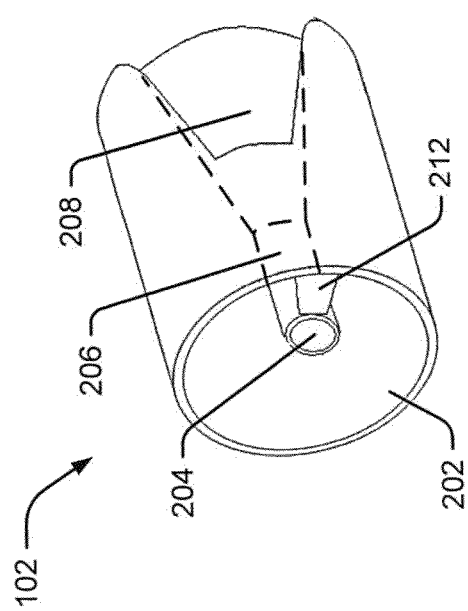
FIG. 2C an isometric view of the inner cap of FIG. 2A taken from the proximal end.

FIG. 2 illustrates three views of inner cap 102. More particularly, FIG. 2A is a schematic view, FIG. 2B is an end view, FIG. 2C is an isometric view taken from proximal end 108, and FIG. 2D is an isometric view taken from distal end 106. Lumen 110 of inner cap 102 includes a working channel 202 and a resection loop channel 204. The dimensions of these channels may vary considerably from one application to another. For example, in procedures where a resected mass is extracted through the tube, working channel 202 may be larger than resection loop channel 204. Otherwise, where no need for removal of a resected mass is presented, resection loop channel 204 may be larger than working channel 202. Moreover, working channel 202 may include numerous other channels to carry desired instruments, such as cameras, light sources, and other endoscopic instruments.

As illustrated in FIG. 2A, resection loop channel 204 extends from proximal end 108 to distal end 106 of inner cap 102. Moreover, a proximal portion of channel 204 may include a hollow or lumenal section 206 (FIG. 2C), and this section may lead to a flared section 208 (FIGS. 2C and 2D) towards the cap's distal end 106.

Section 206 may accommodate an outer sheath of a resection loop (not shown). In one embodiment, the diameter of section 206 is substantially equal to or smaller than the diameter of the resection loop sheath. Moreover, section 206 may taper distally such that the diameter of the section's distal end is smaller than the diameter of the sheath, preventing the sheath from extending beyond the distal end of section 206. Alternatively, section 206 may have a uniform diameter from its proximal to distal end, optionally including a ledge 210 on its distal end. The ledge 210 extends radially inwards, reducing the distal end's diameter to equal the sheath's inner diameter, thereby stopping the sheath from extending distally beyond the distal end of section 206. The shaded portion in FIG. 2B illustrates ledge 210.

It will be understood that instead of the ledge, any other structure may be employed to reduce the diameter of the cylindrical portion's distal portion. For example, some configurations may include actuatable protrusions, or barbs extending inwards in parallel to the distal end of the section 206.

Flared section 208 does not necessarily flare-out radially in all directions; instead, it may flare out parallel to a portion of the cap's internal wall. In some embodiments however, section 208 may fully flare out.

A portion or the entire resection loop channel 204 may be in contact with the inner wall. Alternatively, resection loop channel 204 may be positioned adjacent the inner wall. In this embodiment, a support block 212 may connect resection loop channel 204 with the inner wall. It will be understood that the resection loop channel's placement within lumen 110 may vary without departing from the scope of the present disclosure.

In some instances, section 206 may not abut the inner wall of the inner cap 102. Instead, it may be slightly spaced from the inner surface. Flared section 208, however, may make contact with the inner wall. Moreover, the width of flared section 208 may be smaller than or equal to the diameter of section 206. To maintain this width and to increase the working channel's area, flared section 208 may curve toward the inner wall. FIG. 2A illustrates this embodiment.

Alternatively, the width of flared section 208 may be greater than the diameter of section 206. In this case, the portion of the resection loop channel wall in contact with working channel 202 may extend parallel to the longitudinal axis of section 206, while, the portion of the channel wall closer to the inner wall may flare out radially to contact the inner wall. FIGS. 3A and 3B illustrate this embodiment. Compared to FIG. 2A, it is evident that this embodiment features a broader resection loop channel 204, while the working channel 202 space is reduced.

In an alternative embodiment, the portion of the inner cap 102 abutting flared section 208 may be cut-out or removed, leaving the resection loop channel with a partial wall. Outer cap 104 abuts flared section 208 (FIG. 1A) forming the remaining wall for resection loop channel 204.

The degree of angular displacement of the distal end of flared section 208 may vary based on numerous factors, such as tensile strength of the resection loop, size of resection loop, or diameter of inner cap 102. It will be understood, however, that flared section 208 may be sufficiently broad and wide to allow the resection loop to open completely into an active position. "Active position" refers to a position in which the resection loop is completely open and its loop diameter is approximately equal to the diameter of inner cap 102.

Alternatively, resection loop channel 204 may not have a cylindrical section, and instead, it may begin flaring from the proximal end 108 of the inner cap 102 (shown in FIG. 3C). It will be understood that the shape of flared section 208 may vary without departing from the scope of the present disclosure. For example, the flare's cross-section may have a generally "U" shape, "V" shape, semicircular shape, semi-elliptical shape, square shape, rectangular shape, or any suitable shape.

In FIG. 2, resection loop channel 204 is permanently fixed in the inner cap and in the gap between the inner and outer caps. In another embodiment, however, resection loop channel 204 may be detachably connected to working channel 202. When the resection loop is not in use, resection loop channel 204 may be removed. In another embodiment, the resection loop channel 204 may be collapsible, i.e., formed of a flexible membrane. When the resection loop is not inserted in the cap, the flexible membrane may rest against the inner wall of inner cap 102 (converting the complete lumen into working channel 202). When the resection loop is inserted, it may push the flexible member away from the inner wall and into the working channel 202. Once the lesion is resected, the resection loop may be retracted, and the flexible member may return to its original position (against the inner wall of inner cap 102). Detachably connecting resection loop channel 204 or incorporating it with a flexible wall increases working channel 202 width, allowing the resection device to extract large resected pieces.

Outer cap 104 includes a general cross-sectional shape similar to that of inner cap 102. An inner diameter of outer cap 104, however, is large enough to fit around inner cap 102. When fit over inner cap 102, distal end 107 of outer cap 104 extends distally beyond inner cap 102. The space between the distal ends of inner cap 102 and outer cap 104 may form a track for guiding the resection loop, such as track 112 shown in FIG. 1B.

FIG. 4 illustrates the track in detail. As shown, track 112 includes the circular-shaped distal surface of inner cap 102, and the inner walls of outer cap 104, extending distally beyond inner cap 102. Further, the track may be sufficiently wide and high to slidably receive a resection loop, such as resection loop 402. Moreover, the distal surface of outer cap 104 may include a support structure 404 such as an edge, ridge, ledge, or rail extending circumferentially inward such that the support structure is wide enough to cover the proximal surface of inner cap 102, thus providing a track surrounded on three sides (top, bottom, and outer edge) and open on one side (inner edge). Alternatively, support structure 404 may include multiple equidistant protrusions extending towards the lumen 110. These support structures allow the resection loop 402 to rest parallel to the distal opening of the EMR cap assembly 100 when the resection loop 402 is extended into track 112. It will be understood that any other structure to maintain the resection loop 402 within track 112 is conceivable and within the scope of the present disclosure.

In one embodiment, the distal openings of both inner cap 102 and outer cap 104 may lie perpendicular to the longitudinal axes of the caps. Alternatively, the distal openings may slant at an acute angle to the longitudinal axes. Because tissues may be present on the esophageal walls, out of the direct path of an endoscope advancing through that organ, the slanted distal opening provides a greater surface area contact between the EMR cap assembly's distal opening and the tissues. It will be understood that the slant angle may vary based on the organ or the procedure. For example, a narrower body organ, such as the esophagus, may call for a distal opening slanted at a greater angle than for wider body organs, such as the stomach.

Resection loop channel 204, along with track 112, forms a path for the resection loop 402. The loop, enclosed within a sheath, may be inserted from the proximal end 108 into the resection loop channel 204. The sheath may extend up to the distal end of section 206. From there, the resection loop may be advanced distally into the flared section 208. Because the channel 204 is flared, the resection loop is provided sufficient space to expand into the active position. Moreover, flared section 208 merges with track 112, allowing the resection loop to slide into track 112 in its active position, such that the loop rests along the circumference of the inner cap's distal opening, between the inner and outer cap.

Pushing the resection loop distally places it in the active position on track 112, while pulling the resection loop proximally, closes the resection loop. Because the resection loop lies in track 112, it closes essentially parallel to the distal opening of the EMR cap assembly. This resection loop configuration allows the EMR cap assembly to grasp and hold flat tissues.

As described in this disclosure, the resection loop is a wire loop device used to cauterize a lesion, polyp, or any other tissue. The cross-sectional diameter of the wire may vary according to the application. In an embodiment, resection loop may be a resecting hook, surrounding a portion of the cap. Further, the resecting hook may have any cross-sectional geometry. For example, the cross-section may be flat, round, or triangular. In another embodiment, the resection loop may be a cauterizing resection loop that is energized by passing electrical energy through the loop. Moreover, the electrical energy may be sufficient to cauterize the tissue swiftly. The cauterizing resection loop may be mono-polar where high frequency electrical current is passed from a single electrode and the patient's body serves as ground or bipolar where high frequency electrical current is passed through the tissue from one electrode to another. It will be understood that instead of electrical energy, any other form of energy now known or known in the future may be supplied to the resection loop to resect the tissue from the organ wall. For example, high heat energy may be supplied, enabling the resection loop to burn the tissue from the organ wall. Similarly, other energy sources, e.g. RF and cryogenic, may be considered without departing from the scope of the present disclosure, in addition, the disclosed EMR cap assembly may be utilized with any suitable cutting device known to those skilled in the art.

The inner and outer caps may be detachably connected, permanently coupled, or formed into an integral component. Detachable connections may include, but are not limited to, snap fit assembly, screw fit assembly, bier-lock assembly, or force lock assembly. For example, a proximal portion of the outer cap's inner wall may include one or more screw threads, while the corresponding portion of the inner cap's outer wall may include corresponding screw threads. After placing outer cap 104 over inner cap 102, the outer cap 104 may be rotated to engage the screw threads of the inner and outer caps 102, 104. In another instance, inner cap 102 may include one or more protrusions along its outer wall, while outer cap 104 may include corresponding grooves on its inner wall. The protrusions may engage with the grooves when outer cap 104 is placed over inner cap 102, snap fitting them in place. It will be understood that other temporary connection techniques are well within the scope of the present disclosure.

Permanent connection methods include gluing or spot-welding, depending on the cap material. Alternatively, these elements may be permanently sealed with a high-strength adhesive, such as epoxy. To form a single component, the EMR cap assembly may be made of a single component that includes a resection loop channel merging into a track parallel to its distal opening. The EMR cap may be formed as a single component by molding, lithography or any other suitable manufacturing technique.

The diameter of EMR cap assembly 100 may be configured to match the requirements of particular applications. In general, a uniform diameter along the length of the device may be preferred for most applications. In situations where tissues are small or when the body cavity is very narrow, a tapered EMR cap assembly may be preferred. Conversely, flared or tapered EMR cap assemblies, may be utilized when the tissues are large or the body cavity is wide.

In some embodiments, EMR cap assembly 100 may change states between a collapsed and an expanded state. For example, while advancing a resecting device in the patient's body, EMR cap assembly 100 may assume a collapsed state, and when the device reaches the cancerous site, end-EMR cap assembly 100 may expand for operation. Expandable devices are well known in the art and require no further elaboration here. For example, end-EMR cap assembly 100 may be formed of distinct longitudinal sections joined to each other by flexible members such as rubber, spring, or elastic. Flexible members allow the distinct sections to slide over each other in the collapsed state and abut each other in the expanded state. EMR cap assembly 100 may also be made of any suitable super elastic or shape memory material, such as, for example, nitinol or shape memory polymers.

The following section describes a resection device that may implement the EMR cap assembly 100 for conducting endoscopic mucosal resection.

Exemplary Resection Device

Figure 5:
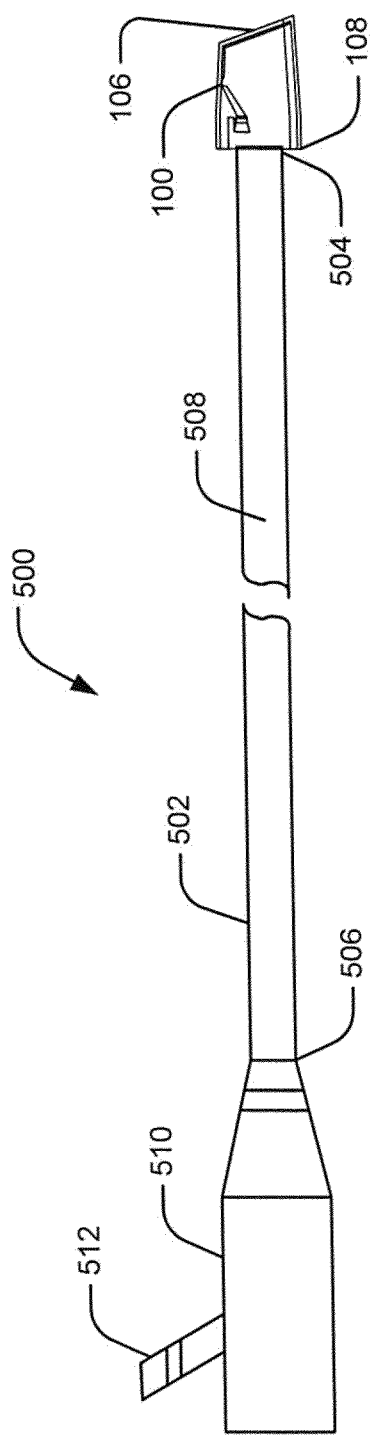
FIG. 5 illustrates an exemplary resection device incorporating the EMR cap assembly of FIG. 1, according to embodiments of the present disclosure.

FIG. 5 is a perspective view of a resection device 500 for cutting and extracting an undesired mass through an incision or a natural body opening. The device 500 includes an elongate tube 502 with a distal end 504, a proximal end 506, joined by a lumen 508. Proximal end 506 may be coupled to a handle 510, while distal end 504 is coupled to EMR cap assembly 100. The tube further includes one or more internal channels (not shown) having proximal and distal end openings.

Tube 502 may have a cross-sectional configuration adapted according to a desired body lumen. In the illustrated embodiment, tube 502 may include a generally circular cross-section, with a generally circular hollow interior lumen. Further, the tube 502 may have a uniform diameter or may be tapered at the distal end to allow convenient insertion within the body.

Depending upon the particular implementation and intended use, the length of tube 502 may vary. For example, tube 502 may be a few centimeters or less where a shallow body cavity or organ is involved. For long cavities or deeper organs such as the bowel or intestine, tube 502 may be relatively long. Similarly, depending upon the particular implementation and intended use, the tube can be rigid along its entire length, flexible along a portion of its length, or configured for flexure at only certain specified locations.

In one embodiment, tube 502 may be flexible, adapted for flexible steering within bodily lumens, as understood in the art. For example, tube 502 can be steered with controls to move at least a portion, generally distal end 504, up and down, or side-to-side. Additional degrees of freedom, provided for example via rotation, translational movement of tube 502, or additional articulation of bending sections, are also contemplated. In such an embodiment, resection device 500 may be provided with suitable steering systems for, among other things, articulating or steering distal end 504 of tube. For example, a suitable steering system may include one or more of pulleys, control wires, gearing, electrical actuators (such as servomotors), pneumatic actuators, and the like.

Such flexible tubes may be formed of any suitable material having sufficient flexibility to traverse body cavities and tracts. Suitable materials may include synthetic plastics, fiber, or polymers. Alternatively, tube 502 may be rigid or semi-rigid, formed from materials such as stainless steel or the like, including super elastic or shape memory alloys such as nitinol. Tube 502 may also be manufactured from any biocompatible material such as a sheath, with or without a Teflon outer layer.

Moreover, the tube 502 and EMR cap assembly 100 may be designed to impose minimum risk to the surrounding tissues while in use. To this end, the proximal or distal ends of these components may include geometrical structures, such as rounded or beveled terminal ends or faces, to reduce trauma and irritation to surrounding tissues. Further, the outer surface of EMR cap assembly and tube may include any suitable coating or covering. For example, the outer surface may include a layer of lubricous material to facilitate insertion through a body lumen or surgical insertion.

To effectively maneuver the tube 502 within a body cavity, the operator should know the exact location of the tube in the cavity at all times. To this end, one or more portions of resection device 500 may be radiopaque, produced by inclusion of material such as barium sulfate in plastic material or one or more metal portions, which provide sufficient radiopacity. Alternatively, the distal end of the tube or EMR cap assembly may include a radiopaque marker or sonoreflective marker (not shown). These markings facilitate detection of a position and/or orientation of tube 502 within the patient's body, and a surgeon, with the aid of suitable imaging equipment, may track the path followed by the endoscope system and avoid potential damage to sensitive tissues. In other embodiments, device 500 is designed to fit through a working channel of an endoscopic device and may be observed through the endoscopic device. Alternatively, the device 500 may be delivered adjacent to or over the endoscopic device.

To inhibit bacterial growth in the body cavity or in the mucosal wall, resection device 500 may be coated with an anti-bacterial coating. The coating may contain an inorganic antibiotic agent, disposed in a polymeric matrix, which adheres the anti-biotic agent to the device's surface. Further, a drug releasing coating may also be applied to the outer surface of resection device 500, assisting in healing. In further embodiments, resection device may be constructed from material impregnated with suitable antibiotic or therapeutic agents.

As discussed, tube 502 may include one or more channels. A typical configuration may include a working channel and a resection loop channel. Based on the application, other channels, such as a scope channel or a camera channel, may also be present. Through these channels, the operator may introduce one or more medical devices to extend out of the distal end of tube 502. For example, during a resectomy, the operator may introduce a suction device into the working channel, and introduce a resection loop into the resection loop channel. Additionally, from time to time during the procedure, the operator may insert a light source, a camera, an injector, or a morcellator within the working channel. The distal ends of these channels may coincide with the working channel and resection loop channel of EMR cap assembly 100 while their proximal end may be coupled to the distal end of handle 510. In other embodiments, light sources and optics, such as a cameras may be integrated into the walls of the tube. Optics may be integrated in the wall of the tube from the proximal end to the distal end. In other embodiment, wireless optic means may be integrated only in the distal end walls of the tube.

The proximal end 506 of tube 502 can be coupled to handle 510 for gripping by an operator such as a surgeon, while the distal end 106 remains open for medical devices to extend out. The handle 510 can be attached to tube 502 by, for example, welding, use of an adhesive, or integrally forming with tube 502.

Handle 510 may include one or more ports 512 to introduce medical devices into the working channels of the tube. Moreover, vacuum pumps or irrigation feeds may be attached to port 512 to generate a suction force at the distal end of the tube, or deliver irrigation fluid to the desired location within a patient's body, respectively. Handle 510 may include ability to steer the distal end of the resection device. Further, the handle portion may include an actuating mechanism to actuate one or more medical devices at the distal end of the elongate tube. For example, the handle may include an actuating mechanism to actuate and close the resection loop at the distal end of the resection device. Similarly, it may include a mechanism to power on or off the suction device attached to its working channel.

The EMR cap assembly 100 may be coupled to the distal end of the tube 502. In one embodiment, the EMR cap assembly 100 may be detachably attached to the distal end of the tube 502 using any known coupling technique such as snap-fitting, luer-lock, screw threading, etc. Before inserting the tube within a patient's body, the EMR cap assembly may be snapped on. Alternatively, the EMR cap assembly may be permanently coupled to the distal end of the tube. Techniques such as gluing, welding, or sealing may be used.

Further, a swivel mechanism may be introduced between the tube 502 and the EMR cap assembly 100, such that the EMR cap assembly 100 may easily swivel to make a greater surface contact with a lesion and swivel towards the lesion. In some embodiments, the cap will swivel upon contact with tissue to allow alignment of the opening of the cap. In other embodiments, the cap may be controllably rotated for aligning the cap opening. Any suitable swivel mechanism may be used without departing from the scope of the present disclosure.

In other embodiments, the tube and the EMR cap assembly may be shaped such that the EMR cap assembly may be inserted into the lumen of the tube until it extends out from the distal end of the tube. Here, the diameter of the tube 502 and the EMR cap assembly 100 may taper from the proximal to the distal end, such that the distal diameter of the tube 502 is lesser than the proximal diameter of the EMR cap assembly 100. In this situation, when the EMR cap assembly 100 is pushed to the distal end, its proximal portion engages with the distal opening of the tube, wedging it in place.

It will be understood that other techniques to engage the proximal end of the EMR cap assembly with the distal end of the elongate tube may be contemplated without departing from the scope of the present disclosure. For example, magnetic connection may be possible between the distal tube opening and the proximal EMR cap assembly opening.

Exemplary Resection Method

FIGS. 6A-6F illustrates a method for resecting lesions or polyps or tissue from a patient's body. A typical location for a resection of this sort is the esophagus, and that location will be discussed here. As will be understood by those in the art, other patient locations would be equally suitable. An endoscopic device including the cap assembly may be inserted into the body lumens either through a percutaneous incision providing access to the esophagus, or through a natural opening, such as the mouth. Once inserted, the resection device 500 is advanced towards a location on a mucosal wall 602. A light source and a camera may be inserted in the working channel to direct the device within the esophagus, and to spot the lesions. Alternatively, polyps and lesions may be identified by any suitable means prior to inserting resection device 500 into the patient. Pedunculated polyps may be easily identified within the esophagus. Low-lying and flat lesions, however, may be harder to discover. To detect these lesions, a biomarker or dye may be sprayed in the esophagus. Cancerous lesions emit a different wavelength when light falls on them, allowing operators to easily detect them.

In the illustrated embodiment, EMR cap assembly 100 is coupled to the distal end of elongate tube 502 when the procedure begins. Alternatively, EMR cap assembly 100 may be actuated to extend out of the distal end of the tube 502 when required. As shown, the distal end of the EMR cap assembly 100 may then be placed over or proximate a lesion 604. In case the lesion is situated at an unreachable position within the body, EMR cap assembly 100 may swivel to attain contact with the lesion and/or surrounding tissue. This position is depicted in FIG. 6B.

The resection loop (not shown) may extend in an open or active state into track 112 when the EMR cap assembly 100 is extended. Next, a suction device is introduced into the working channel of the tube 502 to extend to the working channel 202 of the EMR cap assembly 100 unit. The suction device introduces suction force that draws the lesion 604 into the working channel 202 of the EMR cap assembly 100 (FIG. 6C). In one embodiment, if the lesion is too flat along the esophageal wall, the lesion may be injected with a saline solution or any other suitable solution to create a buffer layer between the lesion and that wall. With the lesion sufficiently raised off the esophagus wall, suction may be more easily accomplished.

Once the lesion 604 is forced into the working channel 202 of the EMR cap assembly 100, the proximal end of resection loop 402 may be pulled proximally, so that resection loop 402 begins closing by withdrawing into track 112, reducing the resection loop's diameter in track 112, and trapping lesion 604. Subsequent pulling may contract resection loop 402 further, forming a tightened grip around lesion 604. This stage is illustrated in FIG. 6D.

In some embodiments, the suction device may be powered off or removed, and a telescope or microscope may be introduced in working channel 202 along with a light device. The scope may closely examine lesion 604 to determine whether it is cancerous or not. Various techniques may be employed for this determination. In one embodiment, a fluorescent or biomarker dye may be sprayed on lesion 604. If lesion 604 is cancerous, it will emit a particular color. Based on the emitted or projected color, physicians can determine whether the lesion is benign or cancerous. Alternatively, by looking at lesion 604 under the microscope, physicians can make this decision.

If desired, an electro cautery device may be inserted in the working channel 202, or the resection loop itself may be a cauterizing resection loop providing electrical energy to the trapped portion of the lesion 604, and resecting it off the esophagus wall (as shown in FIG. 6E). With modifications in the EMR cap assembly 100 device, the electro-cautery device may be replaced with a laser device that resects the lesion. In some embodiments, the cap itself may have electrocautery capability, such as electrodes in the cap. Other resecting means may be contemplated, which will lie within the scope of the present disclosure.

Once the lesion is resected, the device may carry out any one of a number of procedures to remove the resected matter. For example, the resection device 500 may extract lesion 604 or morcellate it and then extract it. For extraction, any retrieval device known now or later may be employed. In one embodiment, the lesion 604 may be extracted with the help of suction force applied at the proximal end of the resection device 500. In another embodiment, a basket, a grasper, or pincers may be used. These devices may be self-expandable or may expand by some actuation mechanism incorporated in the resection device's handle 510. The retrieval device may be inserted in a collapsed state through the proximal end of the tube 502; and, it may extend out of the distal end 106 of the EMR cap assembly's working channel 202 in an expanded state. Once the device is placed over the resected lesion, it may be actuated to close in on the lesion, trapping it. Subsequently, the entire resection device 500 may be withdrawn from the patient's body. In another embodiment, the end of the inner cap may be flexible. After resection, the end of the cap may be actuated to close over the resected lesion, trapping it and subsequently removing it from the patient's body.

If lesion 604 is too large to fit in working channel 202 or be grasped in the other retrieval tools, it may be morcellated prior to extraction. A morcellator (not shown) may be introduced in working channel 202 along with a suction device. The suction device holds lesion 604 around the opening of the EMR cap assembly 100, while the morcellator breaks lesion 604 into smaller pieces. Subsequently, the retrieval devices suction or extract the pieces.

Embodiments of the present disclosure may be used in any medical or non-medical procedure, including any medical procedure where monitoring of an organ's activity is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only with a true scope and spirit of the invention being indicated by the following claims.

What is claimed is:

1. A resection device for resecting tissue from a body, the device comprising:
    an elongate member having a proximal end, a distal end, and a lumen extending between the proximal end and the distal end;
    a cap assembly configured to be coupled to the distal end of the elongate member, the cap assembly comprising:
        a first cap including a resection loop channel and a distal end having a first opening;
        a second cap configured to receive a portion of the first cap, wherein the second cap includes a distal end having a second opening, a distal portion of the first cap and a distal portion of the second cap cooperate to define a resection loop track for receiving a resection loop, and the resection loop track includes a groove formed by a surface of the distal end of the first cap and a surface of the distal portion of the second cap.

2. The resection device of claim 1, wherein the resection loop track and the resection loop channel are in communication with each other.

3. The resection device of claim 1, wherein the resection loop track is disposed in a plane parallel to a plane of the second opening.

4. The resection device of claim 3, wherein the resection loop track extends at an angle to the resection loop channel.

5. The resection device of claim 4, wherein the resection loop channel further includes a resection wire lumen positioned inside the first cap, and fixed at a radially inner surface of the first cap.

6. The resection device of claim 1, wherein the first cap further includes a working channel extending from the distal end to the proximal end of the first cap.

7. The resection device of claim 1, wherein the resection loop channel is formed of a flexible wall configured to collapse the resection loop channel when a resection loop is not present in the resection loop channel.

8. The resection device of claim 1, wherein a portion of the resection loop channel is configured to prevent distal movement of a sheath associated with a resection loop.

9. The resection device of claim 1, wherein the cap assembly is configured to pivot relative to the distal end of the elongate member.

10. An endoscopic cap configured to be secured to a distal end of an introduction sheath, the endoscopic cap comprising:
    a first cap including a resection loop channel and a distal end having a first opening; and
    a second cap configured to receive a portion of the first cap such that a radially outer surface of the first cap faces a radially inner surface of the second cap, wherein the second cap includes a distal end having a second opening, a distal portion of the first cap and a distal portion of the second cap cooperate to define a resection loop track for receiving a resection loop, and the resection loop track is in communication with the resection loop channel and disposed in a plane parallel to a plane of the second opening.

11. The endoscopic cap of claim 10, wherein the first cap further comprises a working channel extending from the distal end to a proximal end of the first cap.

12. The endoscopic cap of claim 10, wherein a portion of the resection loop channel is defined by a radially outer surface of the first cap.

13. The endoscopic cap of claim 12, wherein the resection loop channel further includes a section disposed within the first cap, the section being fixed to a radially inner surface of the first cap.

14. The endoscopic cap of claim 10, wherein the distal portion of the second cap is configured to receive the distal portion of the first cap, and the distal end faces of the first and second caps are angled relative to a longitudinal axis of the endoscopic cap.

15. The endoscopic cap of claim 10, wherein the resection loop is an electrocautery tool.

16. A cap assembly configured to be secured to a distal end of an endoscope, the cap assembly comprising:
    a first cap including (1) a resection device channel extending through a side wall of the first cap, and (2) a distal end having a first opening; and
    a second cap configured to receive a portion of the first cap, wherein the second cap includes a distal end having a second opening, wherein a distal portion of the first cap and a distal portion of the second cap cooperate to define a resection device track for receiving a resection device.

17. The cap assembly of claim 16, wherein the resection device track and the resection device channel are in communication with each other.

18. The cap assembly of claim 16, wherein the resection device track extends at an angle to the resection device channel.

19. The cap assembly of claim 16, wherein the cap assembly is configured to pivot relative to the endoscope.

20. The cap assembly of claim 16, wherein the first cap further includes a working channel extending from the distal end to the proximal end of the first cap, and from the distal portion to a proximal end of the second cap, when the portion of the first cap is received by the second cap.

* * * * *